US010751248B2

(12) United States Patent
Salcido et al.

(10) Patent No.: US 10,751,248 B2
(45) Date of Patent: Aug. 25, 2020

(54) AUTOMATIC CHEST COMPRESSION SYSTEMS THAT INCORPORATE BIOLOGICAL FEEDBACK

(71) Applicant: University of Pittsburgh—Of the Commonwealth System of Higher Education, Pittsburgh, PA (US)

(72) Inventors: David D. Salcido, Pittsburgh, PA (US); Matthew Leo Sundermann, Pittsburgh, PA (US); Robert Theodore Tisherman, Pittsburgh, PA (US); James J. Menegazzi, Pittsburgh, PA (US)

(73) Assignee: University of Pittsburgh—Of the Commonwealth System of Higher Communcation, Pittsburgh, PA (US)

( * ) Notice: Subject to any disclaimer, the term of this patent is extended or adjusted under 35 U.S.C. 154(b) by 1106 days.

(21) Appl. No.: 15/105,510

(22) PCT Filed: Dec. 19, 2014

(86) PCT No.: PCT/US2014/071544
§ 371 (c)(1),
(2) Date: Jun. 16, 2016

(87) PCT Pub. No.: WO2015/095729
PCT Pub. Date: Jun. 25, 2015

(65) Prior Publication Data
US 2016/0317385 A1    Nov. 3, 2016

Related U.S. Application Data

(60) Provisional application No. 61/918,556, filed on Dec. 19, 2013.

(51) Int. Cl.
*A61H 1/00*      (2006.01)
*A61H 31/00*     (2006.01)
*A61N 1/39*      (2006.01)

(52) U.S. Cl.
CPC ......... *A61H 31/006* (2013.01); *A61H 31/005* (2013.01); *A61N 1/3925* (2013.01);
(Continued)

(58) Field of Classification Search
CPC ................ A61H 31/006; A61H 31/005; A61H 2201/10; A61H 2201/123;
(Continued)

(56) References Cited

U.S. PATENT DOCUMENTS 7,645,247 B2    1/2010  Paradis
8,121,681 B2 *  2/2012  Hampton ............. A61H 31/005
                                                        607/5

(Continued)

FOREIGN PATENT DOCUMENTS

EP          1913922      4/2008
WO    WO 2010/004499     1/2010
WO    WO 2013/136231     9/2013

OTHER PUBLICATIONS

International Search Report and Written Opinion for International Application No. PCT/US2014/071544, dated Mar. 30, 2015, 13 pages.

*Primary Examiner* — Steven O Douglas
(74) *Attorney, Agent, or Firm* — Klarquist Sparkman, LLP

(57) ABSTRACT

Automated CPR systems incorporating biological feedback can include an automated compression piston system, a data acquisition system, computer systems for running various control algorithms, ventilation control systems, and/or drug delivery systems. Automated CPR systems can be used as stand-alone systems for treating patients in cardiac arrest, or they can be used to administer pretreatment to a patient prior to defibrillation.

16 Claims, 10 Drawing Sheets

(52) U.S. Cl.
CPC ........ *A61N 1/3987* (2013.01); *A61H 2201/10* (2013.01); *A61H 2201/123* (2013.01); *A61H 2201/1246* (2013.01); *A61H 2201/149* (2013.01); *A61H 2230/045* (2013.01); *A61H 2230/105* (2013.01); *A61H 2230/206* (2013.01); *A61H 2230/207* (2013.01); *A61H 2230/208* (2013.01); *A61H 2230/255* (2013.01); *A61H 2230/305* (2013.01); *A61H 2230/405* (2013.01); *A61N 1/39* (2013.01)

(58) Field of Classification Search
CPC ...... A61H 2201/1246; A61H 2201/149; A61H 2230/045; A61H 2230/105; A61H 2230/206; A61H 2230/207; A61H 2230/208; A61H 2230/255; A61H 2230/305; A61H 2230/405; A61N 1/3925; A61N 1/3987; A61N 1/39
See application file for complete search history.

(56) References Cited

U.S. PATENT DOCUMENTS

| | | | |
|---|---|---|---|
| 2012/0010543 A1* | 1/2012 | Johnson | A61N 1/3925 601/41 |
| 2012/0016179 A1* | 1/2012 | Paradis | A61H 9/0078 600/17 |
| 2012/0116272 A1 | 5/2012 | Hampton et al. | |
| 2014/0236053 A1* | 8/2014 | Walker | C07D 413/14 601/41 |
| 2018/0333097 A1* | 11/2018 | Packer | G06F 19/3418 |

* cited by examiner

AUTOMATIC CHEST COMPRESSION SYSTEMS THAT INCORPORATE BIOLOGICAL FEEDBACK

CROSS-REFERENCE TO RELATED APPLICATIONS

This application is the U.S. National Stage of International Application No. PCT/US2014/071544, filed Dec. 19, 2014, which was published in English under PCT Article 21(2), and claims the benefit of and priority to U.S. Provisional Patent Application No. 61/918,556, filed on Dec. 19, 2013, which is incorporated by referenced herein in its entirety.

FIELD

The present disclosure relates to automated cardiopulmonary resuscitation (CPR) systems and methods incorporating biological feedback for treatment of patients in cardiac arrest.

BACKGROUND

Cardiac arrest is the leading cause of mortality in the United States. The conventional treatment for cardiac arrest includes cardiopulmonary resuscitation (CPR), which involves chest compression and rescue breathing. These actions both aim to keep oxygenated blood circulating throughout the body and preserve the vital organs. Although beneficial, CPR is minimally effective at achieving survival. For example, survival of out-of-hospital cardiac arrest due to CPR has been reported to be only about 7%. There is vast potential to improve the rate of survival in this field.

SUMMARY

Chest compressions that are given during CPR are normally performed manually, but automatic compression devices can provide consistent, effective compressions and do not fatigue. Some automatic chest compression devices for treating cardiac arrest only provide one rate of compression at one depth. However, automatic chest compression devices for treatment of cardiac arrest that can adjust the compression rate and/or compression depth in response to physiological feedback on the effectiveness of CPR can provide more effective CPR and thus superior survival rates to patients. Patients vary widely in their pertinent physical characteristics, such as chest diameter and compliance, and their physiological response to CPR interventions. The automated compression devices and systems described herein can tailor compression depth, rate (and/or other performance parameters) to patient characteristics and responses. Disclosed automated CPR systems can also monitor physiological variables, and particularly cardiopulmonary and/or neurological variables such as blood pressure, blood flow (e.g., measured by Doppler blood flow detection), tissue oxygenation (e.g., cerebral tissue oxygenation), signals from an electrocardiogram or electroencephalogram, coronary perfusion pressure, and signals from ultrasound or related technology (such as echocardiography), to analyze the effectiveness of a certain chest compression depth and/or compression rate and then subsequently change depth, duty cycle, and/or rate until it produces an optimal or desired physiological response.

For treatment of cardiac arrest, desired outcomes can include return of spontaneous circulation (ROSC), survival to hospital discharge (SHD), survival to hospital admission (SHA), survival with good neurological function (SGNF), and successful defibrillation (SD). The systems, devices, and methods described herein can increase the chances of these desired outcomes in a patient suffering cardiac arrest.

The foregoing and other objects, features, and advantages of the disclosed technology will become more apparent from the following detailed description, which proceeds with reference to the accompanying figures.

DETAILED DESCRIPTION

The present disclosure is concerned with systems, devices, and methods for performing automated CPR incorporating biological feedback, such as for treating patients in cardiac arrest, complete cardiac arrest, or other forms of cardiac arrest. The term "complete cardiac arrest" as used herein means the absence of organized myocardial wall motion that circulates blood from the heart into systemic circulation. In certain embodiments, "complete cardiac arrest" includes the absence of residual myocardial mechanical function. Some CPR techniques include manual and mechanical CPR performed according to static performance parameters (e.g., rate=100 compressions per minute, depth=2 inches). These techniques may or may not account for patient-to-patient anatomic or physiologic variability, and may or may not account for changing patient physiology throughout the course of the cardiac arrest, e.g., through the electrical, circulatory, and metabolic stages of cardiac arrest. Systems, devices, and methods described herein can allow for the analysis of physiologic signals from a patient as CPR is being performed and/or can allow for the variation of CPR performance parameters (e.g., compression rate, compression depth, compression force, compression duty cycle, etc.) in order to stabilize, maximize or at least improve the effectiveness of CPR. In general, a system for performing automated CPR incorporating biological feedback can include an automated compression piston system, a data acquisition system, and a computer/control system for receiving input signals indicative of physiologic data from the data acquisition system, analyzing the data using one or more algorithms, and outputting command signals for controlling the automated compression piston system.

Figure 1:
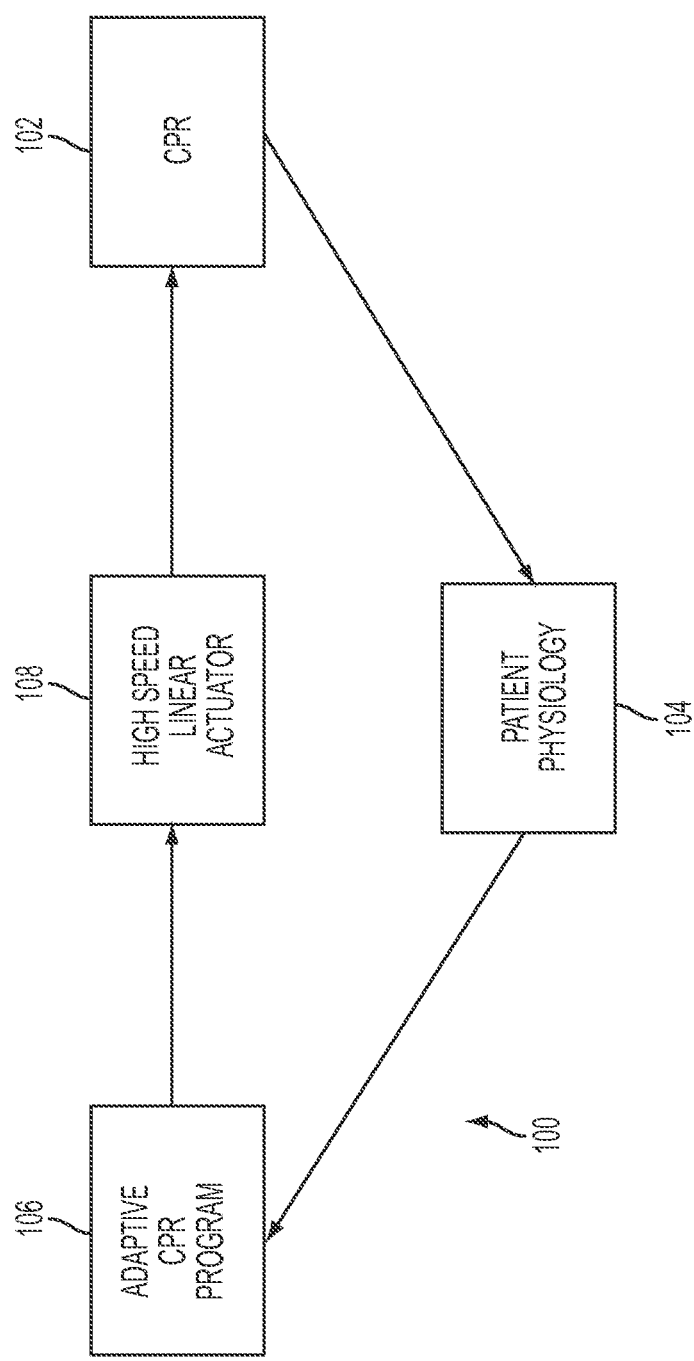
FIG. 1 is a schematic diagram of a closed loop method for the performance of automated CPR incorporating biological feedback.
Figure 2:
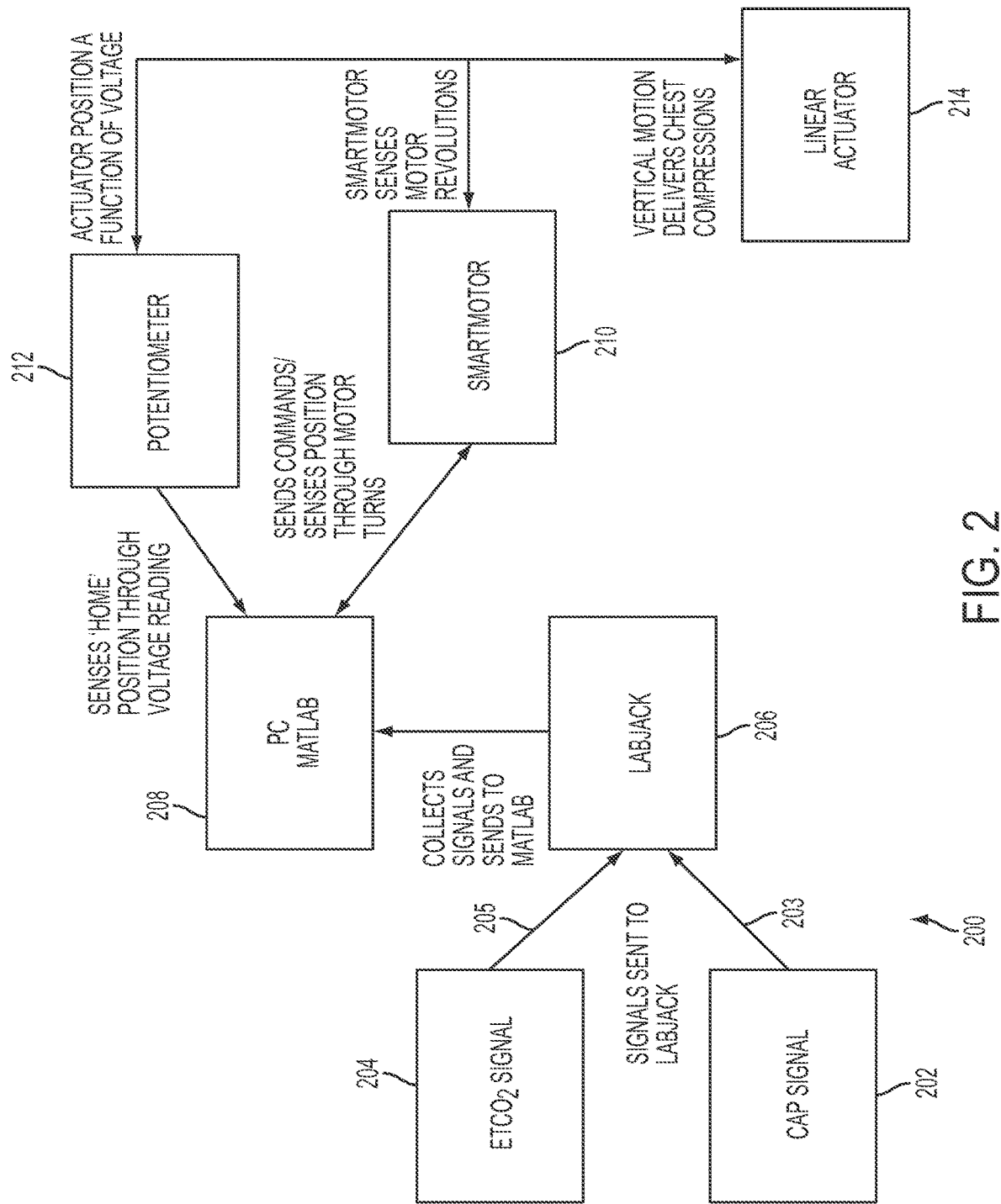
FIG. 2 is a schematic diagram of an automated CPR system and method incorporating biological feedback, illustrating in part that a control system can consolidate physiological signals from a patient and send commands to a motor that moves a linear actuator to generate compressions on the patient.
Figure 3:
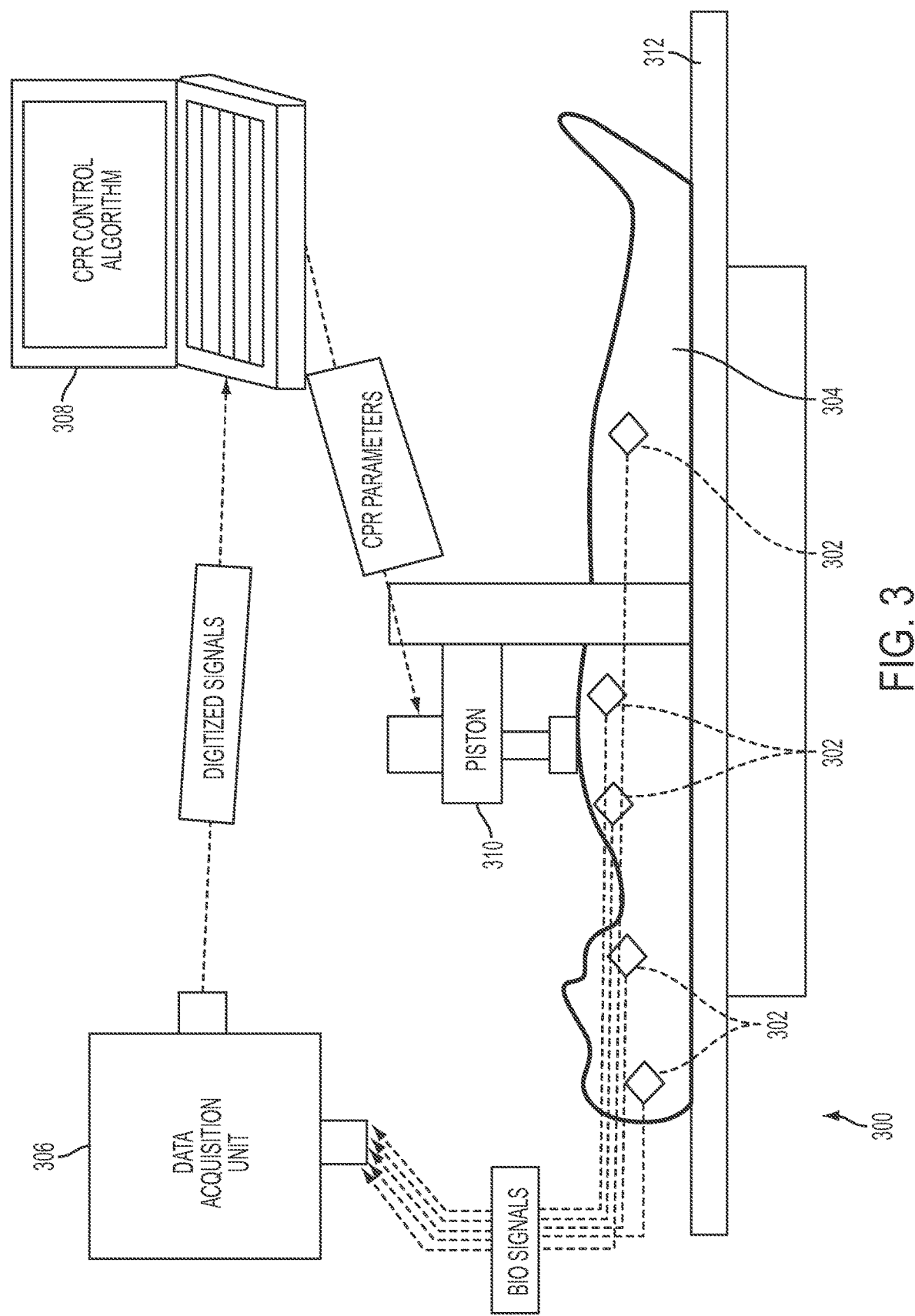
FIG. 3 is a schematic illustration of an automated CPR system that incorporates biological feedback.

FIGS. 1-3 illustrate exemplary systems and methods. FIG. 1 illustrates an exemplary method 100 of performing automated CPR incorporating biological feedback. The method 100 comprises a closed loop of four steps, illustrating the incorporation of biological feedback into the method. Method 100 includes the performance of CPR (e.g., by an automated compression piston system, as described in more detail below) at 102. The performance of CPR at 102 causes changes in the patient's physiology (e.g., increased central arterial blood pressure, etc., as described in more detail below) at 104. The changes in the patient's physiology at 104 are measured (e.g., using a data acquisition system, as described in more detail below) and fed into an adaptive CPR program (e.g., a custom Matlab program, as described in more detail below) at 106, which analyzes the physiologic data and outputs commands to a high speed linear actuator at 108, which controls the characteristics of the CPR performed at 102, thus completing the closed loop method of performing automated CPR incorporating biological feedback.

FIG. 2 illustrates an exemplary system 200 for performing automated CPR incorporating biological feedback. The system 200 includes a sensor 202 for measuring a patient's central arterial blood pressure, which outputs a central arterial pressure ("CAP") signal 203, and a sensor 204 for measuring a patient's end-tidal $CO_2$, which outputs an end-tidal $CO_2$ ($ETCO_2$) signal 205. Additional sensors (including sensors measuring any of the parameters described herein) can be included in the system 200. The signals 203 and 205 are received by a data acquisition device 206, such as a PowerLab device manufactured by AD Instruments or an alternative acquisition device manufactured by Labjack Corporation, which collects the signals and transmits them to a software program 208, such as a custom Matlab program, running on a suitable computing device for analysis. The software program 208, or other software, can receive the signals from the data acquisition device 206, can perform any one or more of various analyses or algorithms, and/or can output command signals to a motor 210 (such as a motor manufactured by Moog, Inc. under the brand name "Smartmotor") controlling a linear actuator 214, which can in turn control the motion of a compression piston for performing chest compressions. The motor 210 can be capable of measuring the number of rotations it has completed and can be capable of transmitting such information back to the software program 208. The system can also include a potentiometer 212 which can provide a voltage reading to the software program 208 indicating the position of the linear actuator 214. Through use of a reference voltage reading from the potentiometer 212 indicating a reference position (e.g., a "home" position), the voltage signal from the potentiometer 212 can indicate to the software program 208 the position of the linear actuator 214.

FIG. 3 illustrates another exemplary system 300 for performing automated chest compressions incorporating biological feedback. The system 300 includes five sensors 302, each measuring a physiologic parameter of a patient 304. The "biosignals" collected by these sensors are transmitted to a data acquisition unit 306, which can collect the data, digitize the signals, and transmit them on to a CPR control algorithm implemented on a computing device 308 (e.g., including a software program such as a custom Matlab program). Based on the results of the control algorithm based on the collected biosignals, the computing device 308 can transmit chest compression parameters to an automated compression piston system 310 which can perform automated chest compressions on the patient 304, at rest on a flat surface 312.

In some embodiments, the automated CPR systems described herein are used to treat patients without any organized or residual cardiac electrical activity. In some embodiments, the systems described herein do not detect a residual myocardial wall contraction of the patient. In some embodiments, the systems described herein do not synchronize action of a compression piston with intrinsic contractions of the myocardial wall that may occur during pulseless electrical activity (PEA) or pseudo-PEA (e.g., they do not time the piston's action to compress the patient's chest during a residual myocardial contraction). Systems and methods described herein can be used to treat a patient in asystole, having no detectable coordinated cardiac electrical activity resulting in cardiac output, ventricular depolarization, cardiac output, and/or myocardial contractions.

Systems, devices, and methods described herein can improve the effectiveness of CPR and thus increase chances of return of spontaneous circulation (ROSC), survival to hospital discharge (SHD), survival to hospital admission (SHA), survival with good neurological function (SGNF), successful defibrillation (SD), and/or other desirable outcomes. Over relatively short time periods, they can aid in the rapid delivery of improved perfusion of blood to vital organs including the heart, thus leading to improved chances of ROSC, e.g., upon defibrillation. Over relatively longer time periods, they can aid in the provision of improved perfusion of blood to the brain, thus leading to improved chances of SHD, e.g., by reducing the impact of global ischemia on the brain during cardiac arrest.

ROSC and SHD are typically desired outcomes for a patient in cardiac arrest. CPR can increase the chances of these outcomes, and other desired outcomes, and its effectiveness in doing so can depend on the characteristics of the blood flow it generates. The characteristics of the blood flow generated by CPR are in some cases correlated with various observable and measurable physiological traits, as described herein. Thus, by measuring such physiological traits and varying CPR performance parameters to improve the traits, chances of ROSC and SHD, and/or other desirable outcomes, can be improved. Systems, devices, and methods described herein can do so more accurately, more consistently, and/or with greater endurance than a person.

Automated Compression Piston System

Figure 4:
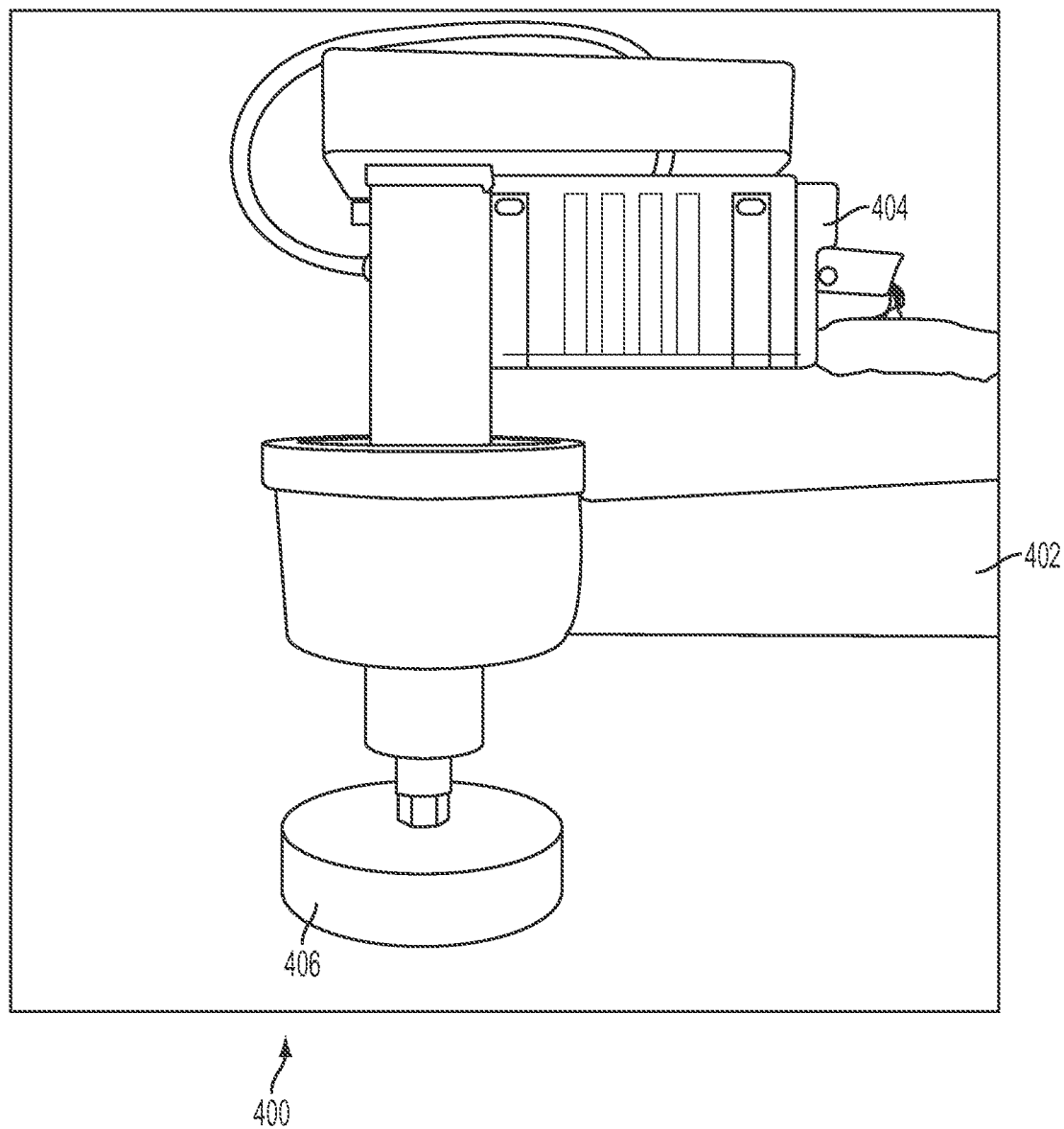
FIG. 4 is an illustration of an exemplary piston for use in the performance of automated CPR incorporating biological feedback.
Figure 5:
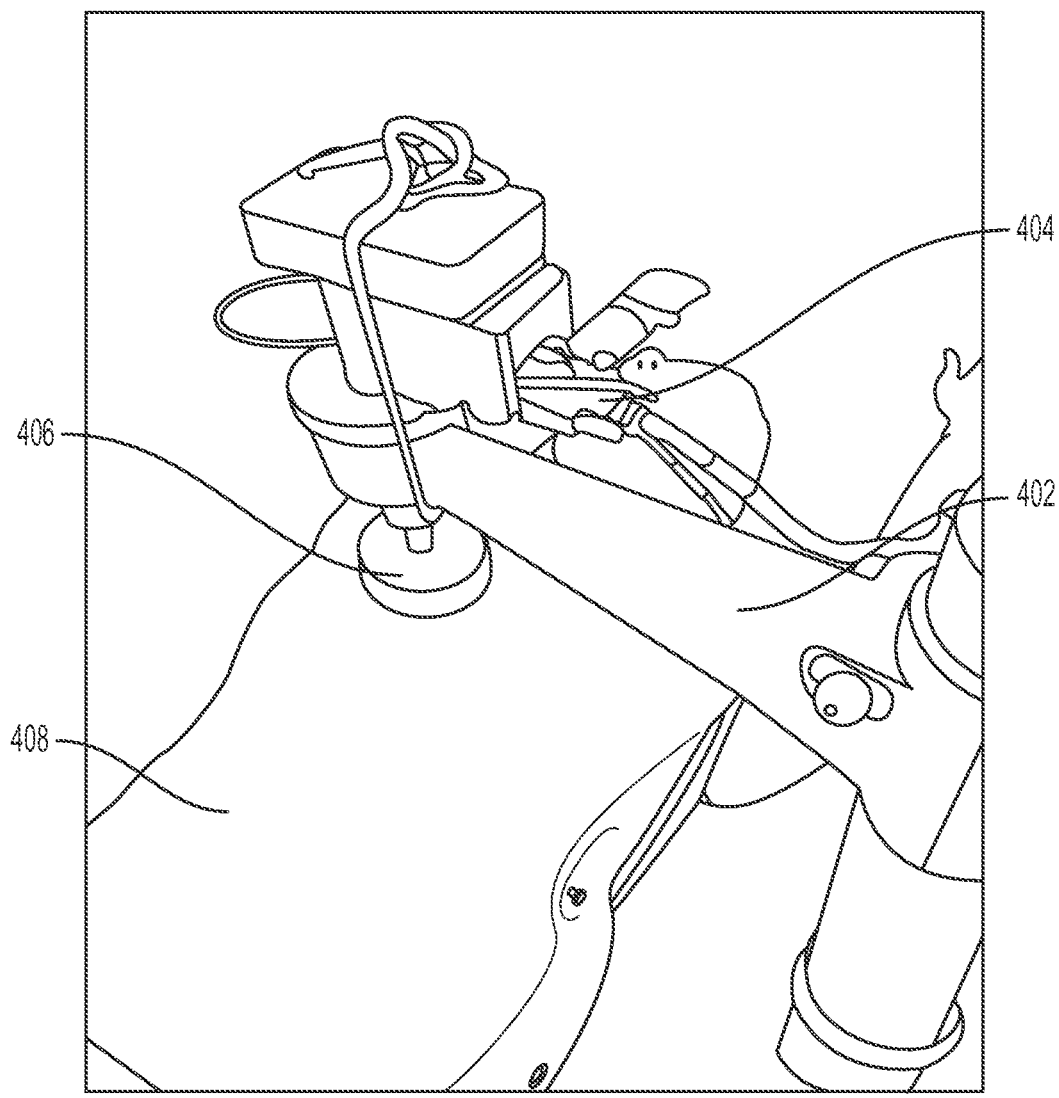
FIG. 5 shows the piston of FIG. 4, positioned over the chest of a patient.

In automated CPR systems described herein, an automated compression piston system can perform the physical action of chest compression, cyclically depressing the patient's sternum to a programmed depth and then retracting at a predetermined cyclic rate. The action of the piston can be periodic and can have a frequency determined by a CPR guidance algorithm. In one specific embodiment, the compression piston is an electric-powered, optically encoded linear actuator driven by a brushless DC motor with a dedicated 48V power supply. One exemplary compression piston system 400 is illustrated in FIG. 4 and includes an arm 402 for reaching over a patient's body, an electrical system 404 for providing power and receiving commands, and a compression plate 406 for imparting forces to a patient's body. FIG. 5 shows the system 400 positioned over and situated to perform CPR on a patient 408.

The function of such a compression piston can also be performed by a pneumatic compression piston, a hydraulic compression piston, a piston powered by an electrical power source, piston powered by internal combustion, and/or a chest compression strap powered by any such means, such as is used in the AutoPulse resuscitation device manufactured by Zoll Medical Corporation. In some cases, the function of this component can be performed by a person, such as in cases where the output of the algorithm can instruct the person of the particular CPR parameters of interest. An automated piston system can be advantageous, however, by providing increased accuracy, consistency, and longevity of CPR application.

The compression plate 406 of the compression piston system 400 can be positioned to be above the patient's heart and/or above the patient's sternum, or can be positioned to be above any suitable part of the patient's anatomy. A compression piston can be provided with a plurality of compression plates 406, each having different diameters or sizes, and the specific compression plate used can be selected, e.g., by a physician, based on the patient's anatomy and/or condition (e.g., there can be various sizes for adults and various sizes for children, infants, and neonates).

An automated compression piston system can be configured to be controlled in various ways. A control algorithm can provide various parameterizations of the desired performance of the piston system. For example, a control algorithm can call for the compression piston to operate cyclically at a desired rate (e.g., compressions per minute) and depth. Another control algorithm can call for the compression piston to operate cyclically at a desired rate and force (which can allow for consistent forces to be imparted on patients having different chest stiffnesses). Other control algorithms can control the velocity with which the piston moves up ("up-speed") and/or the velocity with which the piston moves down ("down-speed"). In one specific example, a control algorithm can call for a specific ratio of up-speed to down-speed to be maintained.

Other control algorithms can control the accelerations of the piston, which can be non-uniform. Other control algorithms can call for a specific duration of exertion of pressure on the patient's body, or a specific duration of no exertion of pressure on the patient's body, or both. In some cases, the compression plate 406 can have an adjustable diameter and/or firmness and the control algorithm can call for changes in the plate diameter and/or firmness over the course of administration of CPR. In cases where the control algorithm calls for the compression piston to operate at a desired force, changing the diameter of the compression plate can produce corresponding changes in the pressure exerted against the patient's chest.

In some cases, the stiffness of a patient's chest can change over the course of treatment with CPR (due, e.g., to fluid movement in the patient's body, breaking of ribs, and/or general changes in the compliance of the patient's tissues). Thus, over the course of the administration of CPR, the force exerted by the piston can be decreased to avoid causing excessive damage, or the depth of compressions can be increased, to maintain constant forces being imparted to the patient's body.

Data Acquisition Unit

A data acquisition unit can sample signals indicative of one or more physiological parameters of a patient and store the signals for analysis by a CPR control algorithm. A general data acquisition unit can acquire any digital or analog signal as a time series of data points, including but not limited to electrocardiography (ECG) signals, expired $CO_2$, $SpO_2$, $StO_2$, blood pressure (for example, mean arterial pressure or mean peripleural pressure as measured by a blood pressure cuff, invasive pressure transducer, or artery waveform by noninvasive tonometry), blood flow (as measured, e.g., by Doppler blood flow detection or ultrasound), tissue oxygen saturation (e.g., pulse oximetry or cerebral tissue oxygenation), temperature, patient chest stiffness, electroencephalography (EEG) signals, quantitative measures of an ECG ventricular fibrillation waveform (e.g., amplitude spectrum area (AMSA), median slope (MS), logarithm of autocorrelation (LAC), or scaling exponent (ScE), described further below), thoracic impedance, pupillary responsiveness, peripheral pulse wave dynamics, or coronary artery perfusion pressure (CPP), blood volume, blood constituent levels, endogenous endocrine or paracrine chemical signals, cellular or mitochondrial energetics and/or function, and the CRP providers spatial, anatomic, or psychological state, as well as any other measures derived therefrom (e.g., a rate of change, mean value, absolute value, integral, frequency, or spectral analysis of those just listed).

In some embodiments, a patient's blood volume can be estimated by introducing dye into the circulation and the concentration of the dye can be measured, such as by optical lasers, to estimate blood volume. Using the patient's blood volume as a parameter for controlling the chest compression device can be particularly useful when the system is used for trauma resuscitation.

In some embodiments, the patient's blood constituent levels, such as levels of electrolytes, leukocytes, antibodies, etc., can be assayed and used as a parameter for controlling the chest compression device. For example, an assay of red blood cells can be used to adjust the chest compressions or other system functions to account for anemia.

In some embodiments, the patient's endogenous endocrine or paracrine chemical signals can be measured. For example, endogenous hormones, catecholamines, etc., can be assayed. Also, an assay of circulating endogenous pressor molecules, such as adrenaline, could feed into an algorithm accounting for expected vascular tone.

In some embodiments, the patient's metabolism, energy stores, cellular or mitochondrial energetics and/or function can be measured. Signals related to such measures can indicate physiologic response or viability during CPR.

In some embodiment, a CPR provider's spatial, anatomic, or psychological state can be monitored. For example, the provider's skin galvanics, limb acceleration, or proximity to the compressor can be measured and used as feedback to the system.

Signals can be acquired secondarily through other devices connected to the patient or directly from sensors attached to the acquisition unit (e.g., pressures can be measured using pressure transducers coupled to the acquisition unit). The signals can characterize the vital state of the patient as a function of the blood flow produced by the device. During complete cardiac arrest, blood flow is suspended due to the cessation or lack of organization of mechanical activity of the heart. Positive effects of CPR can therefore detectable as changes in biosignals that reflect the activity of systems that are receiving blood flow. Since mechanical activity of the heart has ceased or is disorganized, automated chest compressions can be performed without coordinating the chest compressions based on contractions and relaxations of the heart or other residual mechanical activity of the heart, but instead based on other biometrical parameters.

The systems described herein can actively record each of the physiologic signals of interest and organize them to be displayed in a user interface that can be placed near the compression device and patient. The user interface can be capable of tracking the histories of CPR depth and CPR rate and adjustments made thereto, as well as the physiologic signals being recorded. The systems described herein can be configured to collect all signals in a single Matlab™ application for analysis so they can be combined, compared or otherwise analyzed in concert with one another in various ways.

CPR Control Algorithms

In general, suitable CPR control algorithms receive incoming signals (with or without preprocessing) as inputs, and then modulate the performance parameters of the compression piston (e.g., rate and/or depth of compressions) according to a preset strategy (i.e., the algorithm). In one embodiment, the algorithm can be embodied by an interchangeable series of preset strategies. As one simple example (referred to herein as a "threshold algorithm"), while mean central arterial pressure is below a predefined threshold (e.g., as designated by a physician), the device increases chest compression rate and chest compression depth incrementally at fixed time intervals until the desired pressure threshold has been achieved. A similar algorithm can continue to increase compression rate and compression depth until central arterial pressure stops rising in response to increases in compression rate and compression depth. In various embodiments, chest compression rate, chest compression depth, or other CPR performance parameters can be either increased or decreased, as indicated by the patient's condition and the specific control algorithm used.

Any one of various suitable feedback algorithms can be selected (e.g., by a physician based on the patient's condition) prior to the initiation of CPR. In addition to the threshold algorithm described above, a "matching algorithm" can be used to match certain physiologic parameters (e.g., pressures, tissue saturations, etc.) to various compression rates and compression depths based on historic data or previous responses of physiological signals to depth and rate changes. Such an algorithm can reflect the knowledge of vast amounts of historic data collected over time. Such an algorithm can be tailored to the patient's weight and/or chest size, e.g., by initially using a compression depth and/or a compression rate that have historically produced beneficial responses in similar patients.

In some cases, a control algorithm can call for increases in compression depth and/or compression rate until a desired increase in a physiological parameter is observed. For example, a control algorithm can call for increases in compression depth and compression rate until mean central arterial pressure (or coronary perfusion pressure) has increased by 1 mmHg, by 2 mmHg, by 5 mmHg, by 10 mmHg, by 15 mmHg, or by any other suitable pressure. As another example, a control algorithm can call for increases in compression depth and compression rate until mean central arterial pressure (or coronary perfusion pressure) has increased by 1%, 2%, 5%, 10%, 15%, 20%, 25%, 30%, 50%, or by any other suitable amount.

In some cases, a control algorithm can call for the variation of a first parameter (e.g., by either gradual increase or gradual decrease of compression depth) until a first optimal value is found, and then maintenance of the first parameter at its optimal value while a second parameter is varied (e.g., by either gradual increase or gradual decrease of compression rate) until a second optimal value is found, and then maintenance of CPR with the first and second parameters at the respective optimal values. In some cases, a control algorithm can call for the termination of automated CPR when one or more measured parameters indicate the patient is suitable for defibrillation, or when one or more measured parameters indicate the patient is unlikely to recover to such a condition, or when a pulse is measured in the patient (e.g., through the use of any one of various suitable devices, and as one example, through the use of an ultrasound device).

In some cases, physical characteristics of a patient (e.g., height, weight, or chest diameter) are measured and provided to a control algorithm during or prior to initiation of CPR. The control algorithm can determine chest compression parameters based on this information (e.g., based on collections of historic data associating such physical characteristics with advantageous chest compression performance parameters). In some cases, the size of the compression plate used can be selected based on the chest diameter of the patient. In some cases, a control algorithm can be provided with additional input regarding the patient's condition (e.g., whether the patient is suffering from traumatic cardiac arrest or severe hypotension, or whether the patient is especially frail or undergoing concurrent surgical manipulations (e.g., pre-ECMO)), and can optimize the performance parameters based on this information.

A control algorithm can change over the course of the administration of CPR, e.g., to reflect the different stages of cardiac arrest, namely electrical, circulatory, and metabolic. For example, for a patient found to be in the electrical stage of resuscitation, an algorithm can call for the compression piston to work quickly (e.g., at a high compression rate) to provide increased perfusion to the patient before defibrillation is used. For a patient found to be in the circulatory stage of resuscitation, an algorithm can be designed to increase blood flow and/or pressure, in order to help the organs (e.g., the brain) recover from any oxygen deprivation. For a patient found to be in the metabolic stage of resuscitation, an algorithm can be designed to stabilize the patient so he or she can be transported to a medical facility to receive more advanced treatment (e.g., percutaneous coronary interventions (PCI) or extracorporeal membrane oxygenation therapy (ECMO)).

Ventilation Control/Guidance

An automated CPR system can also include a ventilation control or guidance unit to provide or guide ventilation of the patient according to strategies incorporated into a CPR algorithm. Ventilations can be administered to the patient in order to help oxygenate the blood and remove expired carbon dioxide. Complex CPR control algorithms can incorporate ventilation rate, pressure, and volume parameter adjustments to reduce acidosis detected through analysis of expired carbon dioxide or oxygen saturation signals. Ventilation rates, pressures, and volumes can also be adjusted to meet levels complementary to the depth and/or rate of CPR compressions (e.g., the ventilation parameters of ventilation rate and ventilation volume can be synchronized with the compression rate and/or the compression depth). The ventilation unit can include an air pump with an air mix chamber that interfaces with a patient airway adjunct. The ventilation unit can also include a visual or audible readout (i.e. guide) that helps to coordinate a healthcare provider's behavior with the CPR control algorithm's designated ventilation strategy (e.g., in situations where a person is manually performing the ventilation).

Drug Administration/Guidance

An automated CPR system can also include a drug administration control or guidance unit to provide or guide the provision of drugs to the patient according to strategies incorporated into a CPR algorithm. Drugs (e.g., epinephrine) can be administered to a patient during resuscitation in order to increase blood flow generated by CPR, favorably modify the electrical properties of the heart, and/or correct metabolic acidosis. Complex CPR control algorithms can incorporate automatic drug administration via an infusion pump or other custom drug delivery apparatus when deemed appropriate (e.g., by a physician based on the patient's condition). The device can also signal a health care provider to administer a drug according to a drug administration strategy incorporated in a CPR control algorithm (e.g., in situations where a person is manually administering the drugs to the patient).

Automated CPR Prior to Defibrillation

Electrical defibrillation is an established intervention for treating cardiac arrest, but research has shown that the effectiveness of defibrillation decreases rapidly as the duration of cardiac arrest increases. Research has also shown that pretreatment of a patient in cardiac arrest prior to defibrillation can improve the effectiveness of the defibrillation (e.g., it can improve the chances of ROSC), and that the improvements increase as the duration of cardiac arrest increases. In some embodiments, systems, devices, and methods described herein can be used in an independent manner, such as to perform CPR on a patient until native heart function returns spontaneously (until ROSC). In other embodiments, systems, devices, and methods described herein can be used as pretreatment for a patient in advance of defibrillation, as a way to improve its effectiveness.

Research has also shown that the chances of success of defibrillation can depend on certain physiologic parameters of the patient in cardiac arrest. Thus, in cases where automated CPR is performed as a pretreatment prior to defibrillation, it can be useful to provide algorithms that will monitor such parameters, and in some cases discontinue automated CPR and/or alert a physician that these parameters are within a range suitable for initiating defibrillation.

For example, research has shown that the scaling exponent (ScE) of the ventricular fibrillation waveform (a measure known in the art which is understood to increase with duration of ventricular fibrillation) can provide an indication of suitability of a patient for defibrillation. At least one study has concluded that for patients with an ScE less than or equal to 1.20, immediate defibrillation with no pretreatment may be an effective treatment, but for patients with an ScE greater than or equal to 1.3, pretreatment such as CPR prior to defibrillation may be a more effective treatment. Thus, algorithms as described herein can take as input a measure of a patient's ScE and can continue automated CPR until a ScE in the range of 1.2-1.3 is reached, at which point the automated CPR system can terminate CPR and/or alert a physician that defibrillation may be desirable.

Another example is the logarithm of the absolute correlations ("LAC") of the ECG waveform, as presented in a paper titled "Logarithm of the absolute correlations of the ECG waveform estimates duration of ventricular fibrillation and predicts successful defibrillation," (which also discusses the ScE measure) published in the journal Resuscitation, volume 78, pages 346-354 (2008), which is incorporated by reference herein. Similar to the use of the ScE measure described above, algorithms as used herein can take as input a measure of a patient's LAC and can continue automated CPR until an LAC in a predetermined range is achieved, at which point the automated CPR system can terminate CPR and/or alert a physician that defibrillation may be desirable.

As another example, research has shown that coronary perfusion pressure (CPP) can provide an indication of the chances of ROSC with defibrillation. At least one study has concluded that patients with a higher CPP are more likely to experience ROSC upon defibrillation. Thus, algorithms as used herein can take as input a measure of a patient's CPP and can continue automated CPR until a CPP in a desired range is reached, at which point the automated CPR system can terminate CPR and/or alert a physician that defibrillation may be desirable. In some cases, the desired range can be 15 mmHg. In some cases, the desired range can be from 15-25 mmHg. In some cases, the desired range can be from 20-25 mmHg. In some cases, the desired range can be 35-40 mmHg. Various other ranges or related measures can be used, e.g., as determined by a physician based on a patient's condition.

Various other measures of physiologic parameters can be used, together with corresponding predetermined ranges indicating the patient is suitable for defibrillation. Exemplary measures include, for example, mean CPP, cumulative dose CPP, percent recovery of amplitude spectrum area (AMSA), percent recovery of median slope (MS), and percent recovery of LAC, as presented, for example, in a paper titled "Correlation between coronary perfusion pressure and quantitative ECG waveform measures during resuscitation of prolonged ventricular fibrillation," published in the journal Resuscitation, volume 83, pages 1497-1502 (2012).

Exemplary Methods, Tests and Results

Preliminary tests of the devices, systems, and methods described herein have been conducted using a swine model of cardiac arrest. IACUC approved experiments were conducted, in which swine were anesthetized, surgically instrumented with pressure sensors, and electrically induced into cardiac arrest, followed by eight minutes of no treatment to simulate an out-of-hospital patient condition. One pressure sensor was situated in the aorta, and another was situated in the right atrium. Coronary perfusion pressure can be calculated as the difference between the two. Central arterial pressure corresponds to the pressure measured in the aorta, and is presented in the results shown in FIGS. 6 and 7.

An automated CPR system initiated chest compressions following an algorithm calling for an initially low compression rate and an initially low compression depth, with gradual increases to both parameters until a desired central arterial pressure is met. More specifically, the algorithm called for an initial compression depth of 1.4 inches and an initial compression rate of 105 compressions per minute (CPM). The algorithm called for an increase in compression rate of 5 CPM every 20 compressions. When 100 total compressions had been performed, the rate was not increased by 5 CPM. When 120 total compressions had been performed, the algorithm called for the rate to be decreased to 100 CPM and the depth to be increased by 0.2 inches. When 300 total compressions had been performed, the rate was not increased by 5 CPM. When 320 total compressions had been performed, the algorithm called for the rate to be decreased to 100 CPM and the depth to be increased by another 0.2 inches, to 1.8 inches.

Figure 6:
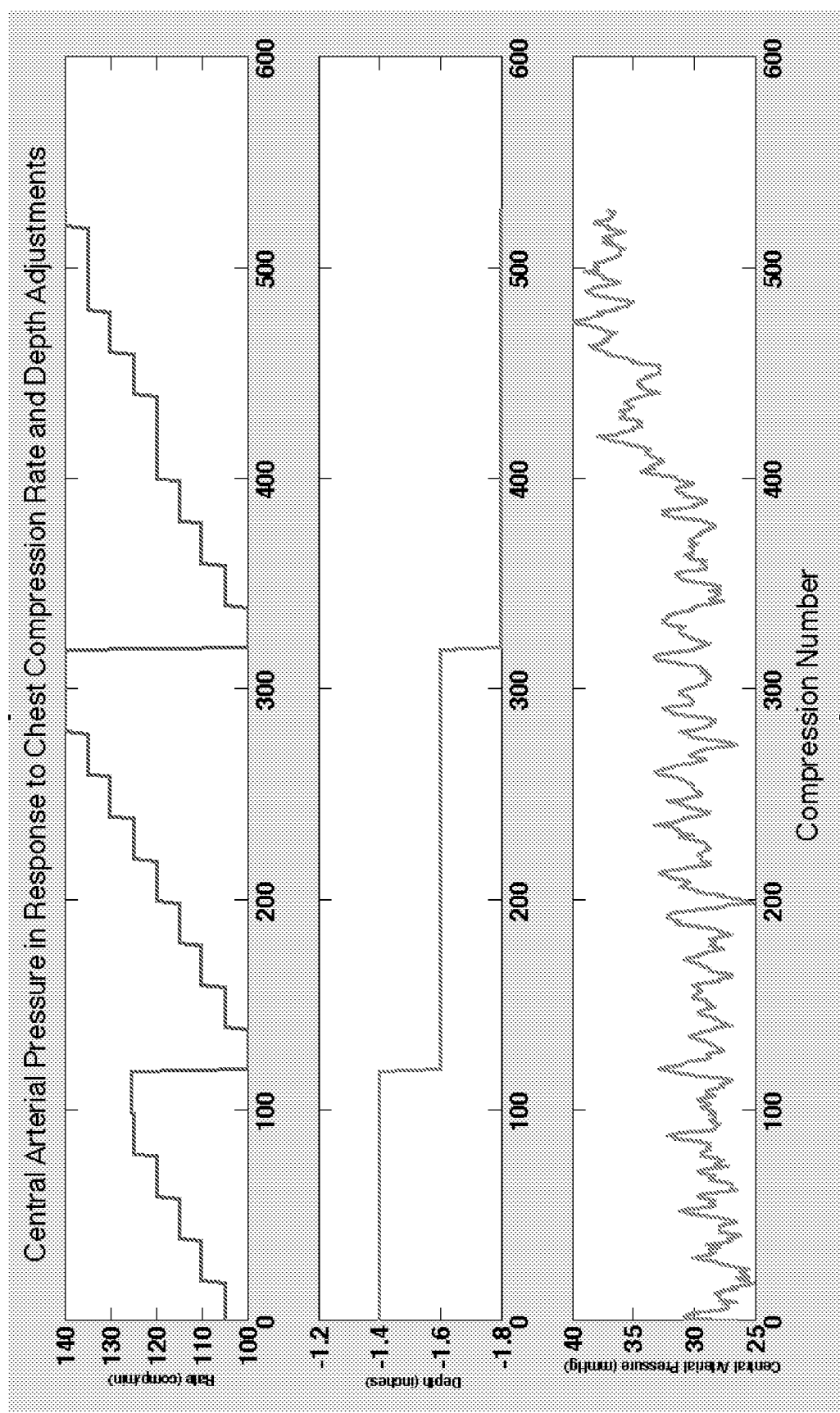
FIG. 6 is a chart plotting compression rate (in compressions per minute) and compression depth (in inches) of an automated CPR system, together with resulting central arterial pressures (in mmHg), illustrating in part that higher pressures result when rate and depth are increased.

As shown in FIG. 6, the data illustrates that central arterial pressure increased significantly after the compression depth was increased to 1.8 inches and as the compression rate was increased. Systolic and diastolic values increased producing an increase in the mean central arterial pressure. The pressure data is shown in greater detail in FIG. 7. After the central arterial pressure increased significantly, the algorithm called for the compression rate and compression depth to be held steady. Increased central arterial pressure is desirable for patients in cardiac arrest as it can signify increased blood perfusion and thus increased oxygen to vital organs. Other algorithm(s) and physiologic signal(s) are effective in achieving the desired physiologic response to automated CPR and can be used.

Figure 7:
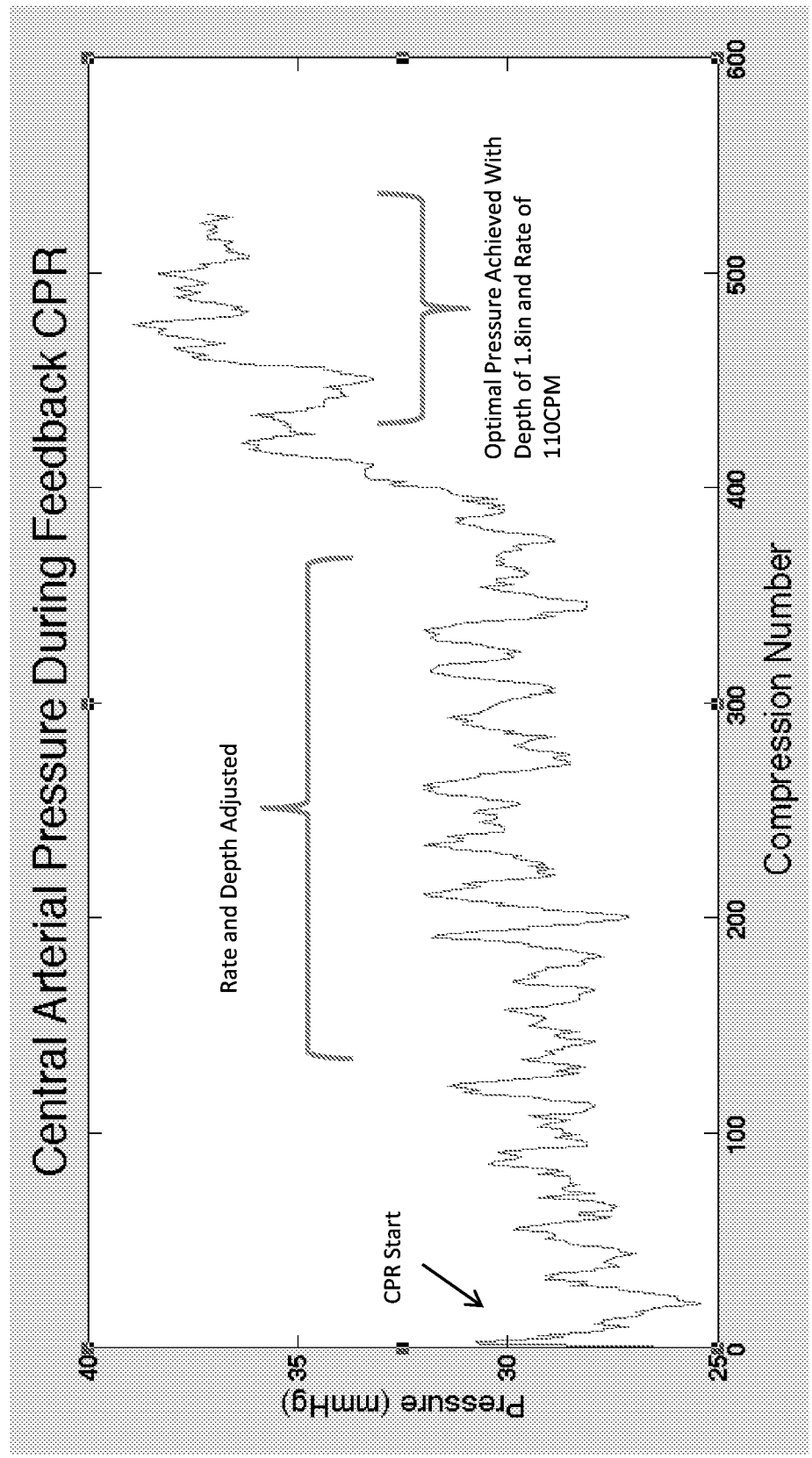
FIG. 7 is a chart plotting the central arterial pressure data of FIG. 6.

The data shown in FIGS. 6 and 7 illustrate that the systems and methods described herein can improve hemodynamics (e.g., central arterial pressure) in a patient suffering from cardiac arrest. Such improvements can increase chances of both ROSC and SHD. When used with human patients, similar compression algorithms can be used. As illustrated in FIG. 6, one such algorithm begins at an initial low compression rate and low compression depth, increasing the compression rate incrementally until a predetermined maximum rate is reached (e.g., 125 CPM), at which point the compression depth is then increased and the compression rate is reset to the initial low compression rate. These steps can be repeated until desired changes in physiologic parameters are detected, such as the increase in central arterial pressure show at the right of FIG. 7. In the illustrated example, an optimal pressure is achieved with a compression depth of 1.8 inches and a compression rate of 110 CPM.

Figure 8:
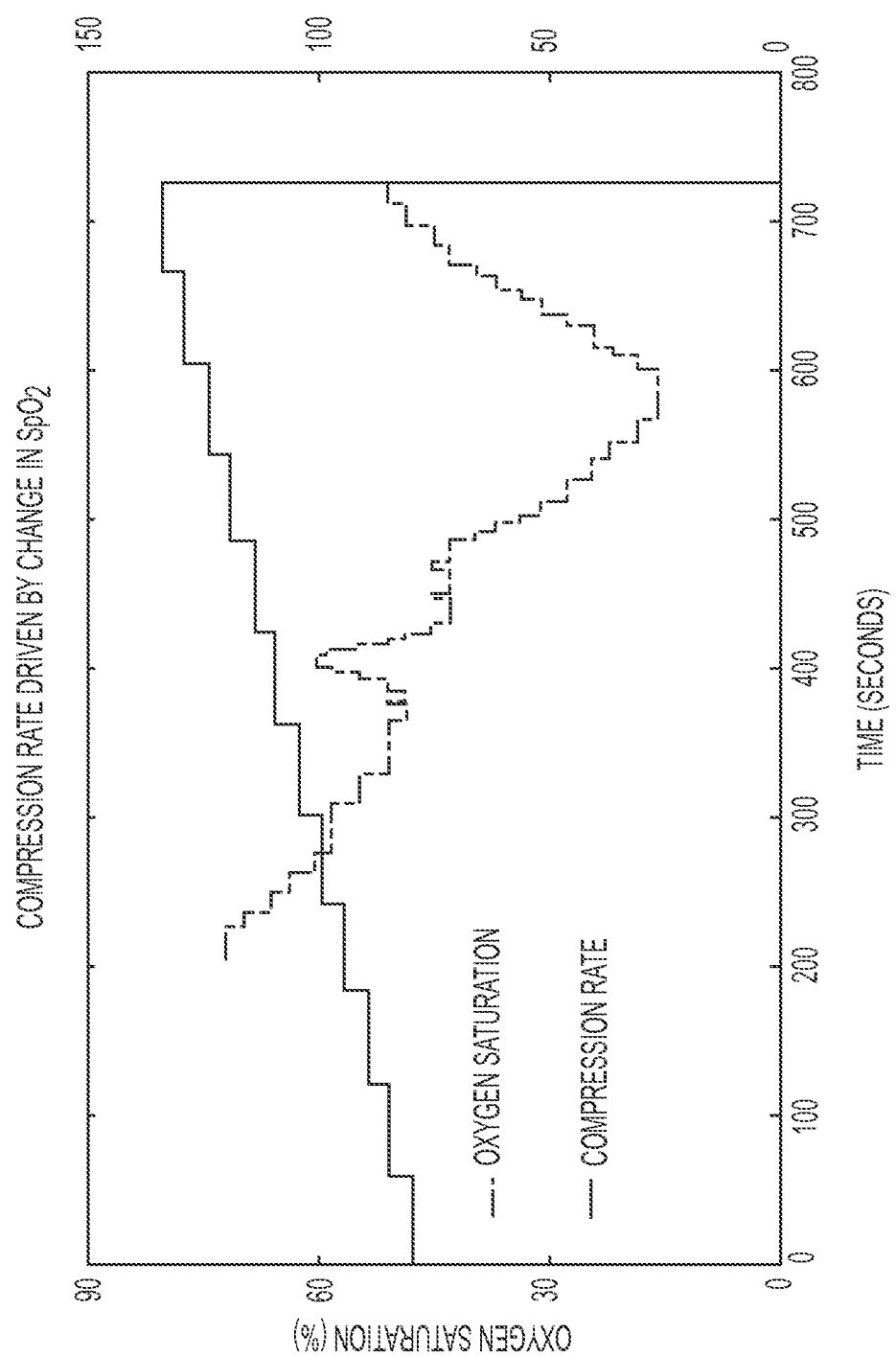
FIG. 8 is a chart plotting compression rate (in compressions per minute) and patient oxygen saturation (in percentage) versus time for an exemplary CPR method, illustrating in part that compression rate can be increased in intervals until a desired oxygenation threshold is achieved.

FIG. 8 shows data from an exemplary swine cardiac arrest model where physiologic pulse oximetry ($SpO_2$) responded to changes in compression rate. The onset of CPR begins at the far left of FIG. 8. Chest compression rate (right vertical axis) is gradually increased while compression depth is kept constant until a favorable, increasing response is observed in the pulse oximetry signal, shown as oxygen saturation % on the left vertical axis. A pulse oximetry or oxygen saturation percentage threshold can be set, such as a predetermined percentage or a predetermined increase in percentage, and once that threshold is met, the compression rate adjustments can stop and/or the compression rate can decrease. This method is an example of an algorithm approach where one CPR parameter is dependent on one physiologic signal and alterations are made using a threshold-based algorithm.

Figure 9:
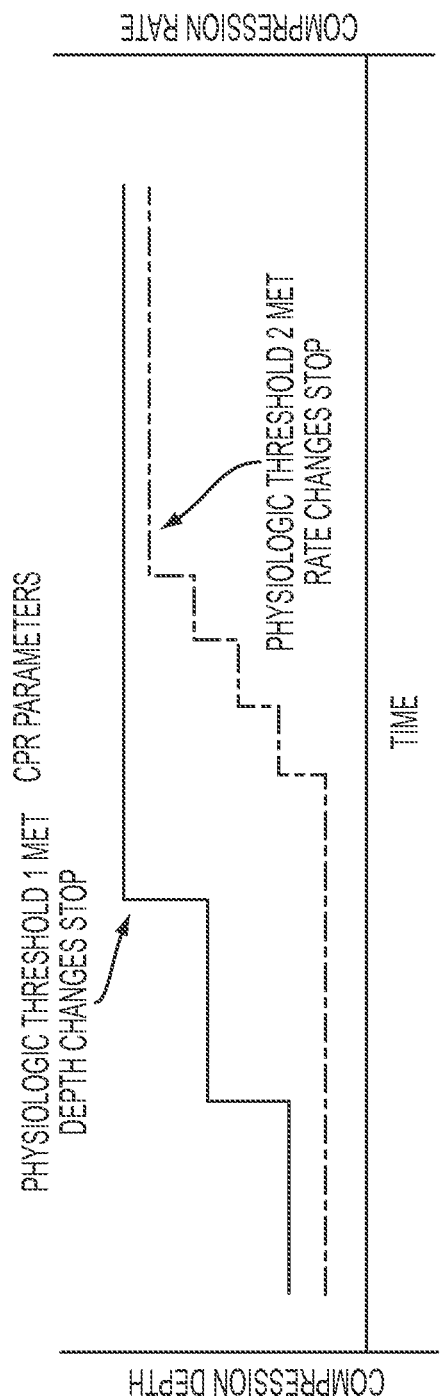
FIG. 9 illustrates a method wherein compression depth is increased in intervals over time until a first physiological threshold is met, and then compression rate can be increased in intervals over time until a second physiological threshold is met.
Figure 10:
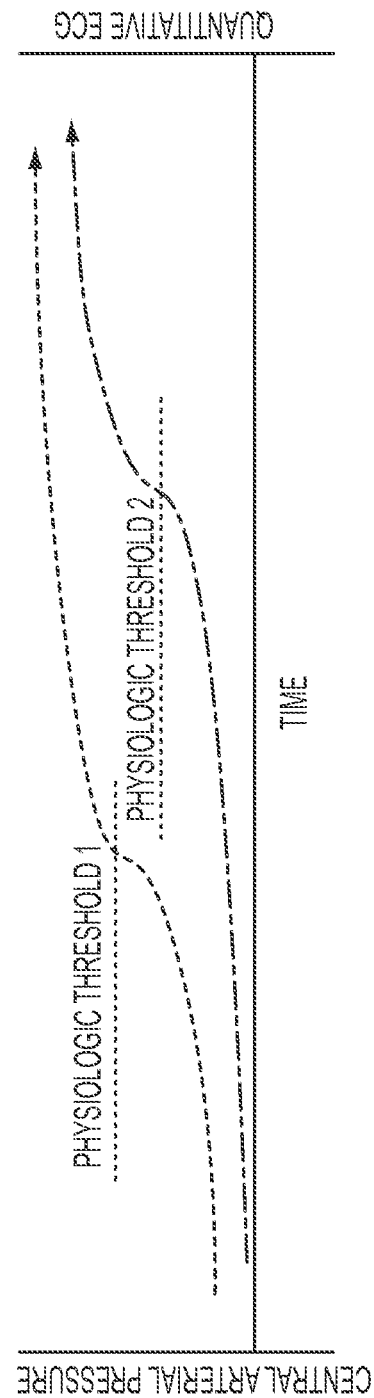
FIG. 10 corresponds to the method of FIG. 9, and illustrates an example where the first physiological threshold is related to central arterial pressure and the second physiological threshold is related to a quantitative ECG measurement.

FIGS. 9 and 10 illustrate exemplary methods in which chest compression depth and chest compression rate are adjusted until two different physiologic thresholds are met. In the methods illustrated in FIGS. 9 and 10, chest compression depth can be adjusted (e.g., increased in increments) until a central arterial pressure threshold, or other physiologic threshold ("physiologic threshold 1"), is met, signaling a positive response to compression depth change, and chest compression rate can be adjusted (e.g., increased in increments) until a quantitative ECG parameter threshold, or other physiologic threshold ("physiologic threshold 2"), is met, signaling a positive response to compression rate change. The adjustments to compression rate can be performed after the adjustments to compression depth are performed, as illustrated. For example, adjustments in depth can stop before adjustments in rate begin, or vice versa. In other methods, the adjustments to rate and depth can overlap or occur at the same time. FIGS. 9 and 10 illustrate an example of a general methodology wherein multiple physiologic signals are utilized in order to drive multiple adjustments in CPR performance. In the example of FIGS. 9 and 10, two physiologic signals are monitored and analyzed at the same time, and depth and rate are adjusted in response to the two signals.

Figure 11:
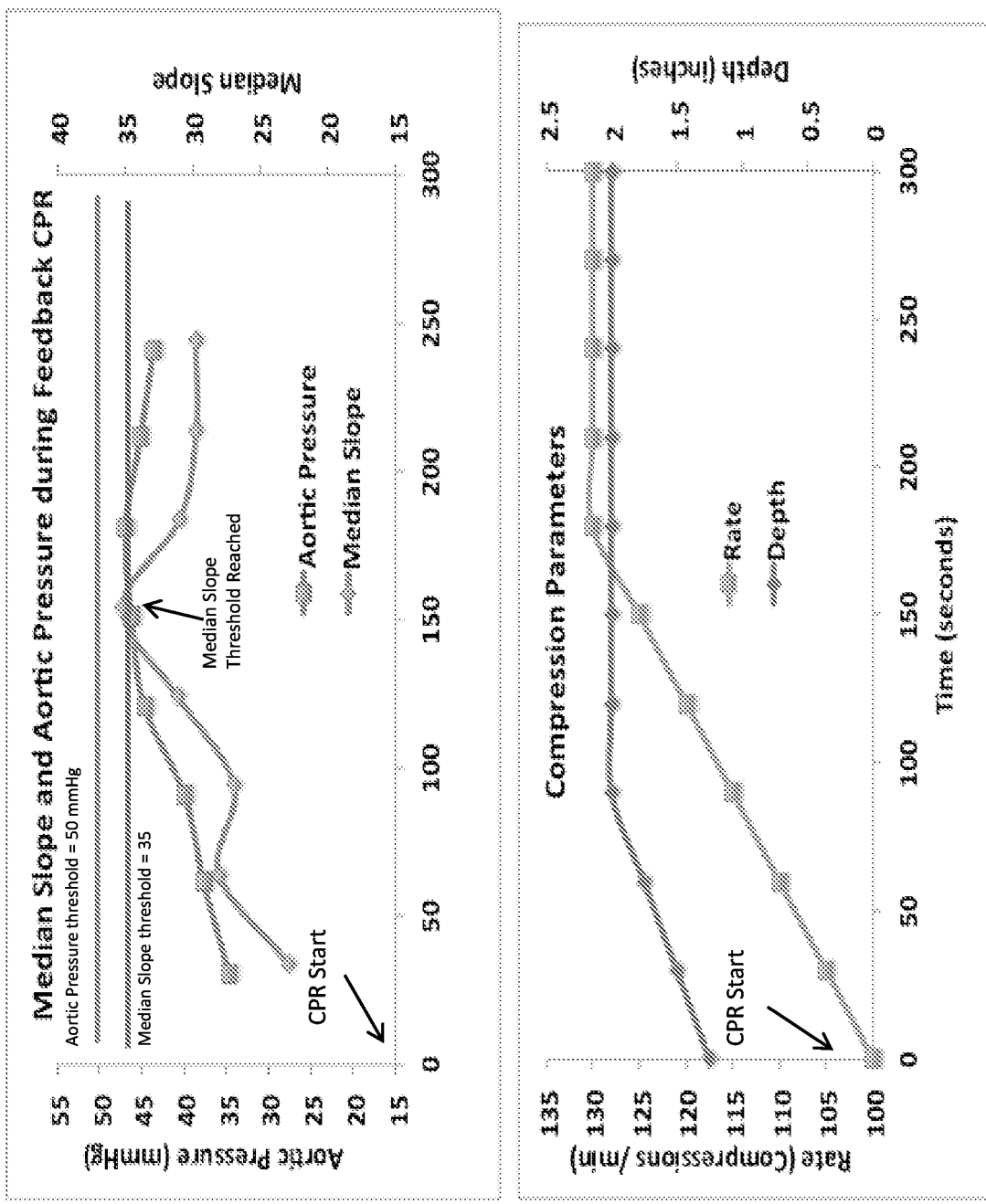
FIG. 11 illustrates a method wherein two different chest compression parameters (rate and depth) are adjusted over time (see lower graph) until one of two biosignals thresholds (one threshold for aortic pressure and one threshold for median slope of ventricular fibrillation waveform) are met (as shown in upper graph).

FIG. 11 illustrates a method wherein two different chest compression parameters (e.g., rate and depth) are adjusted over time (see the lower graph) until one of two biosignal thresholds (e.g., one threshold for aortic pressure and one threshold for median slope of ventricular fibrillation waveform) are met (as shown in the upper graph). In FIG. 11, CPR begins at Time=0. The compression depth and compression rate are gradually adjusted (increased) over time during CPR until either aortic pressure reaches 50 mmHg or median slope reaches 35. As illustrated in the lower graph of FIG. 11, compression depth increases to a maximum of about two inches after about 100 seconds and then is held steady, while compression rate increases from about 100 CPM to about 130 CPM after about 180 seconds and then is held steady. As shown in the upper graph of FIG. 11, the result of these adjustments to compression depth and rate is that aortic pressure and median slope gradually increase over time until median slope meets the threshold of 35. Once the median slope threshold is met, compression rate adjustment stops and the rate is held steady. In such a method, the achievement of either one of two biometric thresholds can indicate that an optimal, desired, and/or sufficient combination of compression depth and compression rate has been achieved.

Any algorithms and/or methods disclosed herein may be performed using or with software, computing hardware, and/or firmware, such as can be stored or included in a computer processing device, volatile or non-volatile memory, and/or computer readable media, which can include non-transitory, tangible, non-propagating, and/or other types of computer readable media.

In view of the many possible embodiments to which the principles disclosed herein may be applied, it should be recognized that the illustrated embodiments are only preferred examples and should not be taken as limiting the scope of the disclosure. Rather, the scope of the disclosure is at least as broad as the following claims. We therefore claim all that comes within the scope and spirit of these claims.

The invention claimed is:

1. A cardiopulmonary resuscitation (CPR) system comprising:
   a computing system comprising a control algorithm, the computing system being capable of executing the control algorithm, wherein the computing system is operable to receive an input signal comprising input data and transmit an output signal comprising output data, wherein the control algorithm determines the output data based on the input data;
   a data acquisition system including a sensor operable to measure a physiological parameter of a patient in cardiac arrest, the data acquisition system being operable to transmit the input signal comprising the input data to the computing system, wherein the input data includes an indication of the physiological parameter of a patient during cardiac arrest; and an automated compression piston system including an actuator operable to perform automated chest compressions on the patient and capable of automatically adjusting the depth of the chest compressions, the piston system being operable to receive the output signal comprising the output data from the computing system, wherein the output data includes a parameter specifying adjustment of the depth of the chest compressions performed by the piston system based on the physiological parameter;

wherein the computing system is configured to gradually increase the depth of chest compressions administered by the compression piston system to a patient over time until a predetermined threshold value for the physiological parameter of the patient is measured by the sensor.

2. The system of claim 1, wherein the system is configured to perform the automated chest compressions without coordinating the chest compressions based on contractions and relaxations of the heart or other residual mechanical activity of the heart.

3. The system of claim 1, further comprising a patient ventilation control system in signal communication with the computing system and operable to perform patient ventilation based on output data from the computing system, wherein the output data further includes a parameter specifying desired action of the patient ventilation control system, and wherein the desired action of the piston system is synchronized with the desired action of the patient ventilation control system.

4. The system of claim 1, further comprising a drug administration system in signal communication with the computing system and operable to perform drug administration to the patient based on output data from the computing system.

5. The system of claim 1, further comprising a defibrillator in signal communication with the computing system and operable to perform defibrillation on the patient based on output data from the computing system.

6. The system of claim 5, wherein the physiological parameter of the patient indicates whether the patient is suitable for defibrillation.

7. The system of claim 1, wherein the piston system is in signal communication with a defibrillator monitor and capable of exchanging data with the defibrillator monitor.

8. The system of claim 1, wherein the physiological parameter is a cardiopulmonary parameter.

9. The system of claim 1, wherein the physiological parameter is a neurological parameter.

10. The system of claim 1, wherein the physiological parameter includes one or more of the following parameters:

the patient's electrocardiography signal;
the patient's electroencephalography signal;
the patient's expired $CO_2$;
the patient's $SpO_2$;
the patient's $StO_2$;
the patient's blood pressure;
the patient's blood flow;
the patient's tissue oxygen saturation;
the patient's cerebral tissue oxygenation;
the patient's temperature;
the patient's chest stiffness;
the patient's thoracic impedance;
the patient's pupillary responsiveness;
the patient's peripheral pulse wave dynamics;
the patient's ventricular fibrillation waveform;
the patient's coronary artery perfusion pressure;
the patient's blood volume;
the patient's blood constituent levels;
the patient's endogenous endocrine or paracrine chemical signals; and
the patient's cellular or mitochondrial energetics or function.

11. The system of claim 1, wherein the system is capable of detecting one or more conditions of the patient that indicates that the patient has a pulse, and determining whether automated chest compressions from the piston system should cease based on the detected one or more conditions.

12. A method of treating a patient in cardiac arrest, comprising:

increasing depth of chest compressions administered to the patient over time until a first physiological parameter threshold of the patient is met, and then maintaining constant chest compression depth; and increasing a rate of chest compressions administered to the patient over time until a second physiological parameter threshold of the patient is met, and then maintaining constant chest compression rate.

13. The method of claim 12, wherein the depth and rate of the chest compressions is controlled by an automated chest compression device in communication with a control system that monitors the first physiological parameter of the patient and the second physiological parameter of the patient.

14. The method of claim 12, wherein the first physiological parameter is central arterial pressure of the patient.

15. The method of claim 12, wherein the second physiological parameter is a quantitative ECG parameter of the patient.

16. The method of claim 12, wherein the increasing of the rate of chest compressions is performed after the increasing of the depth of chest compressions is performed.

* * * * *